United States Patent
Anitua Aldecoa

(10) Patent No.: US 8,142,190 B2
(45) Date of Patent: Mar. 27, 2012

(54) SET OF MOTOR-DRIVEN INSTRUMENTS TO AID THE FIXING OF DENTAL IMPLANTS

(75) Inventor: Eduardo Anitua Aldecoa, Vitoria (ES)

(73) Assignee: Biotechnology Institute, I Mas D, S.L., Victoria (ES)

( * ) Notice: Subject to any disclaimer, the term of this patent is extended or adjusted under 35 U.S.C. 154(b) by 0 days.

(21) Appl. No.: 12/779,430

(22) Filed: May 13, 2010

(65) Prior Publication Data

US 2010/0273128 A1    Oct. 28, 2010

Related U.S. Application Data

(62) Division of application No. 10/526,187, filed as application No. PCT/ES03/00443 on Sep. 2, 2003, now abandoned.

(30) Foreign Application Priority Data

Sep. 2, 2002  (ES) .................................. 200202006
Nov. 18, 2002  (ES) .................................. 200202646

(51) Int. Cl.
  *A61C 3/02* (2006.01)
  *A61C 9/00* (2006.01)
(52) U.S. Cl. ...................................................... 433/165
(58) Field of Classification Search .......... 433/172–176, 433/165, 215, 141, 166
See application file for complete search history.

(56) References Cited

U.S. PATENT DOCUMENTS

| | | | |
|---|---|---|---|
| 4,990,088 | A | 2/1991 | Weissman |
| 5,525,314 | A | 6/1996 | Hurson |
| 5,944,525 | A | 8/1999 | Ura |
| 6,068,480 | A | 5/2000 | Misch et al. |
| 6,179,616 | B1 | 1/2001 | Danger |
| 6,290,499 | B1 | 9/2001 | Lazzara et al. |
| 6,319,005 | B1 | 11/2001 | Hollander et al. |
| 6,854,972 | B1 | 2/2005 | Elian |
| 2002/0094508 | A1 | 7/2002 | Lorenzi |
| 2002/0172923 | A1 | 11/2002 | Strong et al. |
| 2003/0087217 | A1* | 5/2003 | Coatoam ....................... 433/173 |

FOREIGN PATENT DOCUMENTS

| | | |
|---|---|---|
| DE | 4326841 A1 | 2/1995 |
| ES | 2 067 209 | 3/1995 |
| WO | 9803130 A1 | 1/1998 |
| WO | 9917676 A2 | 4/1999 |
| WO | 9918881 A1 | 4/1999 |
| WO | 02/24102 A1 | 3/2002 |

* cited by examiner

*Primary Examiner* — Cris L Rodriguez
*Assistant Examiner* — Heidi M Eide
(74) *Attorney, Agent, or Firm* — Browdy and Neimark, PLLC

(57) ABSTRACT

Set of motor-driven instruments to aid the fixing of dental implants that combines drills (1, 2) and motor-driven osteotomes (4A, 4B, 4C, 4D) of progressive diameters. These have a threaded conical section (9), followed by a threaded cylindrical section (8) and another area (7) to fit the connectors (14, 17) to the surgical motor or a manual extractor.

8 Claims, 4 Drawing Sheets

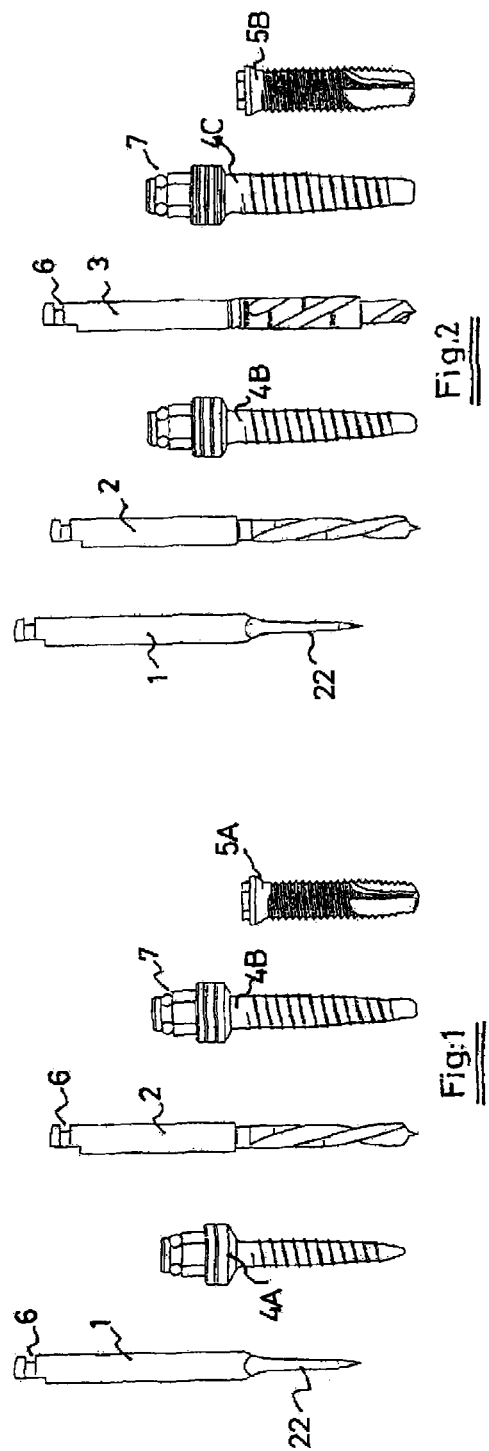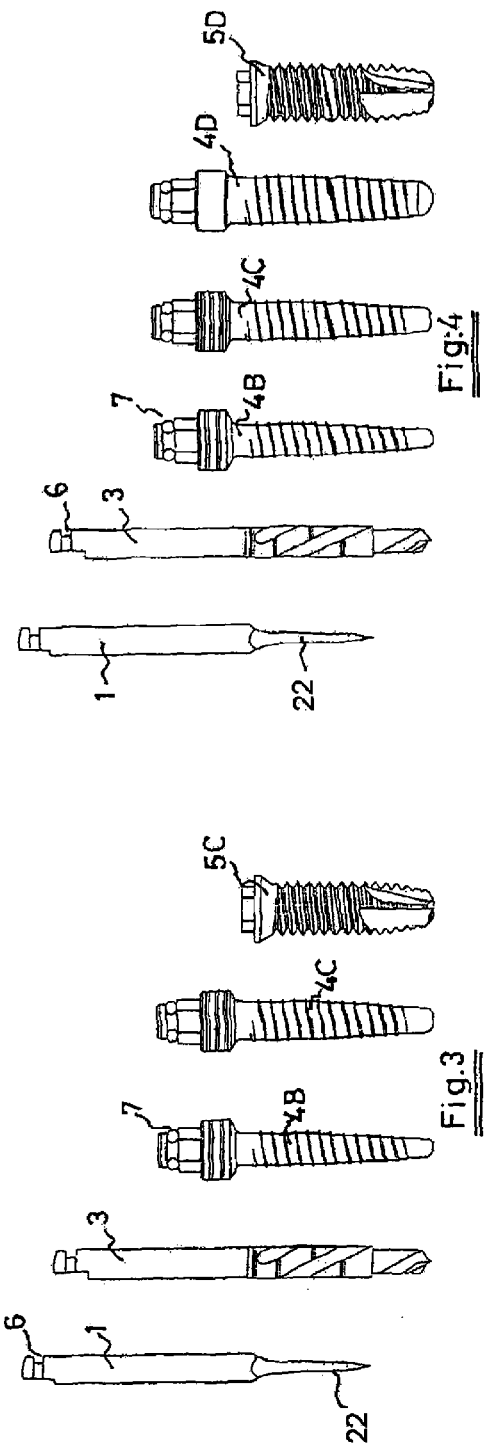

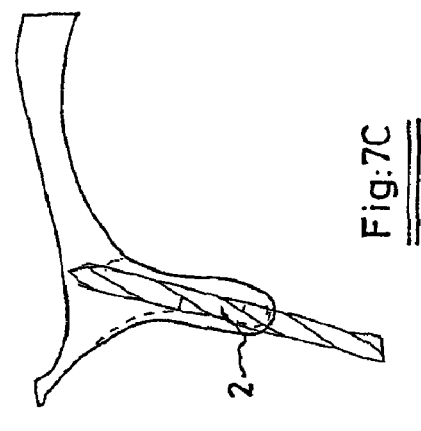
Fig:7A
Fig:7B
Fig:7C
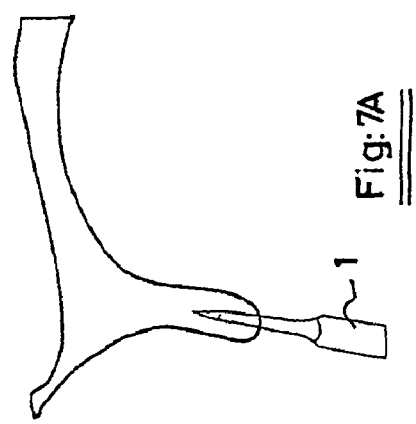
Fig:7D
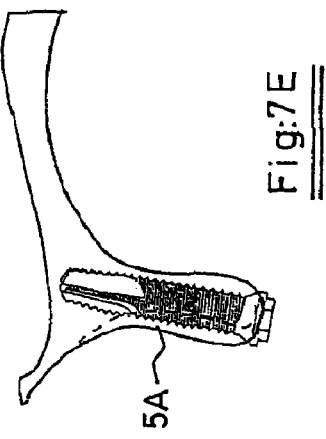
Fig:7E

SET OF MOTOR-DRIVEN INSTRUMENTS TO AID THE FIXING OF DENTAL IMPLANTS

CROSS-REFERENCE TO RELATED APPLICATIONS

The present application is a division of application Ser. No. 10/526,187, filed Oct. 25, 2005 (now abandoned), which is a 371 national phase of international application no. PCT/ES03/00443, filed Sep. 2, 2003 which claims priority of Spanish patent nos. ES/P200202006, filed Sep. 2, 2002 and ES/P200202646, filed Nov. 18, 2002. The entire contents of prior applications are incorporated herein by reference.

DESCRIPTION

The invention relates to a set of motor-driven instruments to aid the fixing of dental implants, in particular to those instruments used in bone expansion, bone compaction or sinus elevation techniques; techniques designed to modify in a suitable way the bone structure that receives the implant before it is finally fixed in position. This set of instruments includes atraumatic bone osteotomes consisting of a series of members with a conical apical zone and with progressive diameters, which are individually and successively introduced into the bone and then extracted using suitable manual means.

Some traditional osteotomes known in the prior art are described in the publication, "A New Approach to Surgery and Prosthesis on Implants" (Dr. Eduardo Anitua, 1996), in the cases that describe the fixing of implants in the area at the front of the upper maxillary bone in cases of bone type 3 or 4, i.e. spongy or cancellous bone, with the conducting beforehand of a phase of expansion of the bone crest that will house the implant. The process to expand the crest and fix the implant is based on the alternate use of osteotomes or instruments in the following way: the process begins with the use of an instrument whose function it is to mark the start point or insertion point where an implant is to be fitted; the crest of the bone is then expanded by pressing in the appropriate instrument, always by hand, with it even being necessary to use a hammer if the bone is compact.

Then, with other osteotomes of a greater diameter the aim is to expand the crest until a suitable floor is created to allow the implant to be inserted, for example an implant of 3.3 mm, as suggested in WO 0224102 awarded in favour of this applicant.

In short, in this way an implant can be inserted using only manual osteotomes successively.

The instruments or manual osteotomes used in techniques to expand narrow bone crests can also be used to impact against and compact the bone, a technique that is necessary when the bone onto which the implant is to be fixed is cancellous, for example, an area at the rear of the upper maxillary of bone type 4. The process for conducting this technique is generally similar to the expansion technique, with the exception that at a specific moment the surrounding bone is compacted or condensed as a result of the application of osteotomes of a larger diameter.

As regards the atraumatic elevation of the sinus, the procedure usually commences with an initial phase in which incisions are made with the first two osteotomes down to the floor of the sinus, and then proceeding with the elevation of the sinus by using successive osteotomes and also introducing bone graft material into the base.

The formal characteristic of these instruments known and used in the aforementioned techniques is that they usually have a cylindrical or conical form similar to that of the cores of the implants used, in order to obtain good stability that ensures that the implants are inserted with excellent results.

As mentioned above these traditional techniques were published by Dr. Eduardo Anitua in 1996 under the title, "A New Approach to Surgery and Prosthesis on Implants". The disadvantage of these techniques, all of them manual, is that they cannot be used on the lower jawbone or in areas at the rear of the maxillary bone, and furthermore if the bone is very compact (types 1 or 2), tapping must be carried out with a hammer, which is very painful for patients.

In addition ES 2127116 B relates to a set of expanders that, it is claimed, prevent problems deriving from osteotomes (with osteotomes being understood in this document as punches that are tapped on the dental base by a small hammer in an erroneous interpretation of the prior art from 1996). However, the disadvantage of these expanders is that they do not meet the objectives they were designed to achieve and they do not give rise to properly stabilised fixing of the implants, as bone-implant inconsistencies are created that derive from their specific form not being adapted to that of the final implant to be inserted. Furthermore they are introduced by manual means, keys etc; and their combined use with drills is not intended.

For the purposes of overcoming the drawbacks of the instruments and known manual techniques, it is an object of this invention to provide a set of osteotomes and drills of a new design that can be used alternately, with all of them motorised and driven by a surgical motor.

By using motor-driven instruments, and applying a known and controlled torque, crests can be expanded in areas at the rear of the maxillary bone or in areas at the front and rear of the lower jawbone and in any type of bone.

It is another object of this invention to provide a set of instruments that allow better directional and torque control than common techniques.

It is another object of this invention to provide a set of instruments that allows crests to be expanded, creating a greenstick fracture in extreme cases, preventing total fracture and the loss of the vestibular plate, which is the case in the aforementioned ES 2127116 B.

In order to reach these objectives and with a view to their correct interpretation, five sheets of drawings are attached in which the following is represented:

FIGS. 1 and 2 show two examples of implant-fixing procedures with prior bone expansion using the inventive motor-driven instruments.

FIGS. 3 and 4 show two examples of implant-fixing procedures with prior bone compaction using the inventive motor-driven instruments.

FIGS. 7A to 7E show the sequence of application of the procedure in FIG. 1.

FIG. 8A-D shows an example of an implant-fixing procedure with prior elevation of the sinus using the inventive motor-driven instruments.

FIGS. 1 to 4 show that, according to the invention, the implant-fixing procedures both with prior bone expansion (FIGS. 1 and 2) and prior bone compaction (FIGS. 3 and 4) begin always with the use of a starter drill (1). One end (22) of this starter drill (1) acts on the patient's bone whereas its other end (6) receives a surgical motor to drive it. The end (22) is narrow and short and has a quadrangular section, characteristics that endow the starter drill with optimal qualities for piercing the hardest outer layer of the bone.

Other drills (2, 3) of different sections can also be fitted to the surgical motor, and are used to define the directional depth and other parameters of the cavity housing the implant. The use of the drills (2, 3) is alternated with the use of the osteotomes (4A, 4B, 4C and 4D) with different-sized cross sections, which are applied gradually depending on the type of bone in question, the purpose of the action (expansion or compaction) and the size of the final implant.

The ends of the inventive osteotomes adopt similar geometries to those of the different implants (5A, 5B, 5C, 5D), with a threaded conical area followed by another cylindrical area, as can be seen in greater detail in FIGS. 5 and 6 below.

Figure 5:
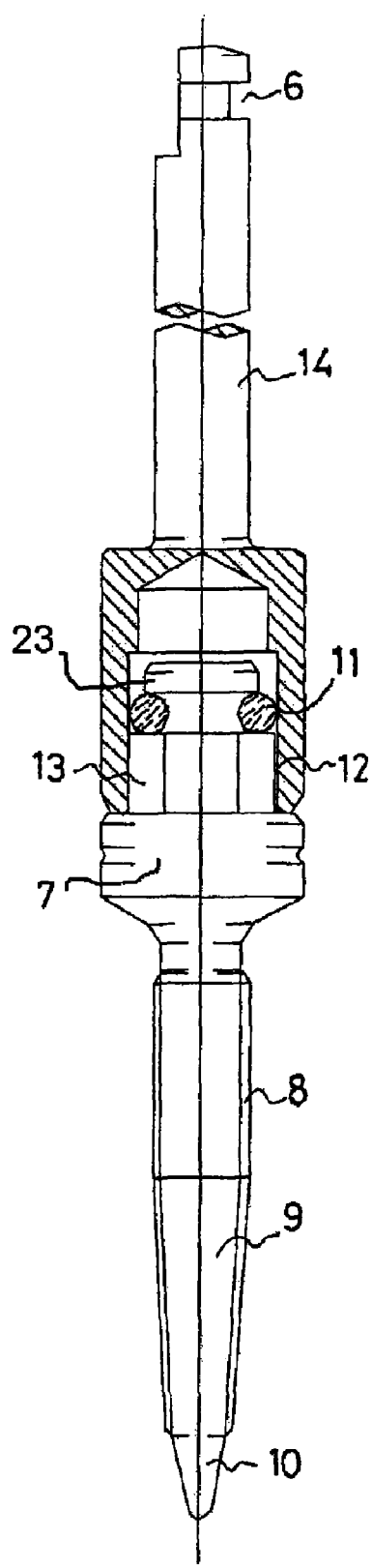
FIG. 5 shows an elevation in cross section of an osteotome assembled to a connector connected to the surgical motor, according to the invention.
Figure 6:
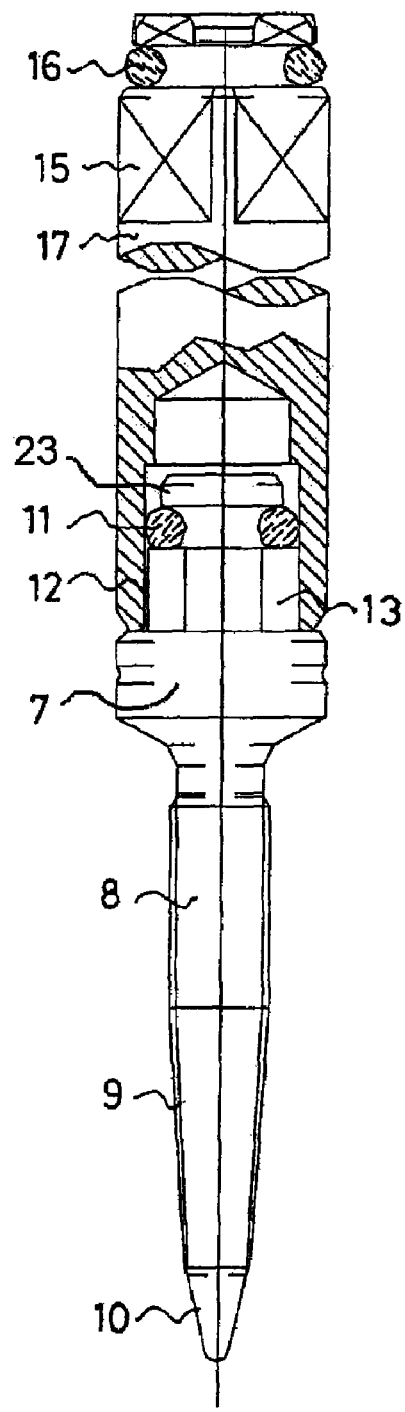
FIG. 6 shows an elevation in cross section of an osteotome assembled to a safety connector connected to the ratchet wrench, according to the invention.
Figure 8A:
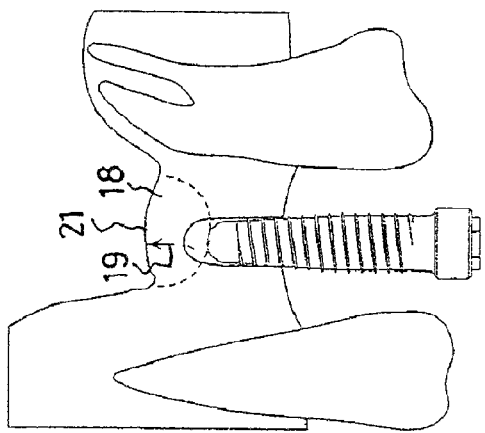
Figure 8B:
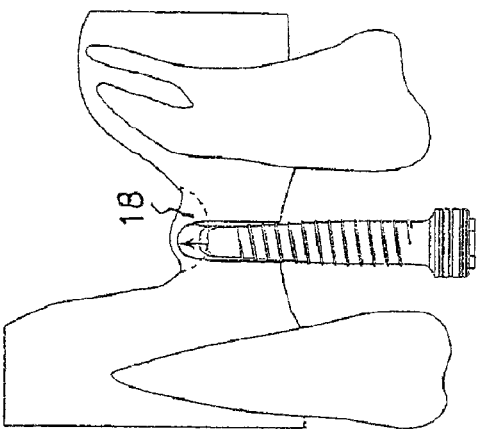
Figure 8C:
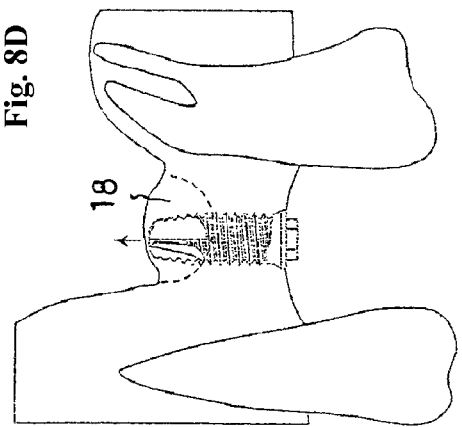
Figure 8D:
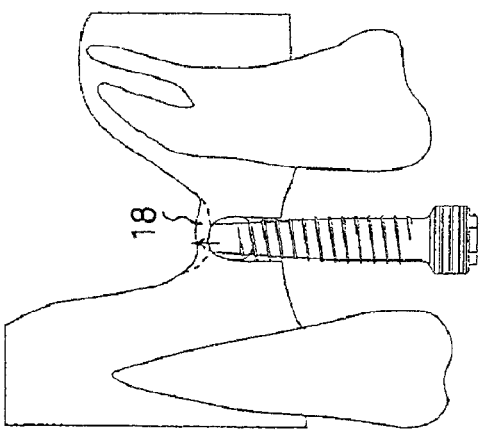

With regard to the coronal ends or adjustment areas (7) of the osteotomes, these are partly designed in order to receive connectors to the surgical drive motor or to a manual extractor (for example a ratchet wrench), all of which is also defined in FIGS. 5 and 6.

In these units in FIGS. 1 to 4, the final implants are of different dimensions. Thus, the implant (5A) measures 3.3×15, the implant (5B) 3.75×15, the implant (5C) 4.5×15 and the implant (5D) 5×15.

FIG. 5 shows the design of an osteotome and a connector (14) according to the invention, as well as the assembly between both. With regard to the design of the osteotome, this presents an apical end (10) from which extends a threaded conical section (9) followed by a threaded cylindrical section (8).

Next, the coronal end or adjustment area (7) is capped by a polygonal projection (13) in its cross section upon which rests an O-ring seal (11) held in position by a rivet (23).

Upon the adjustment area (7) is assembled the connector (14), which has an end (6) that can be connected to the surgical motor, as is the case with the aforementioned drills. The connector comprises, on its opposite end, a blind axial recess (12) with a polygonal cross section that coincides with that of the polygonal projection (13) of the osteotome, so that the connector fits around the osteotome.

In order to keep this assembly between parts stable, the O-ring seal (11) comes into contact with the inside of the connector (12) so that when the connector fits around the polygonal projection (13) of the osteotome, the seal acts as a member maintaining and retaining the assembly so that the two elements cannot be inadvertently detached while they are being handled.

In the event that it is necessary, for whatever reason, to remove an osteotome that has become stuck inside the bone in which it has been disposed, reference shall be made to the arrangement described in FIG. 6. In this arrangement it can be seen that the connector (17) is provided with a free end in which an O-ring seal (16) can be seen disposed in proximity to a coupling area (15) in which the hand ratchet wrench is fitted to allow the osteotome to be extracted without difficulty.

The O-ring seal (16) has the same function as the O-ring seal (11), i.e.—to prevent the ratchet wrench from separating from the connector.

The inventive osteotomes present a conical/cylindrical geometry with a progressive cross section, and as a result they act as wedges that gradually cause the crest to expand. Because of this progressive form, an excellent location is also created for the implants that have a very similar form to that given to the osteotomes.

The drills, used in combination and alternately with the osteotomes, enable the crest to be expanded, for example, in a lower maxillary or upper maxillary bone comprising very compact bone, for example, in bone types 1, 2 or 3.

In addition, the use of the surgical motor implies greater control of the torque, considerably more control of the direction in addition to better control of the force to be applied.

FIGS. 7A to 7E show a typical example of the working method with the inventive set, specifically with the set represented in FIG. 1, based on the starter drill (1), the osteotome (4A), the drill (2), the osteotome (4B) and finally the implant (5A), measuring 3.3×15 in this proposal. In this typical example the hardest outer layer of the bone is pierced by the starter drill (1), to be followed by a process to expand the bone and define the cavity housing the implant carried out as a result of the combined use of the tools (4A, 2, 4B), and to be completed with the fitting of the implant (5A).

The representations in FIG. 8 show how the atraumatic elevation of the maxillary sinus is conducted, protecting the sinus membrane (21) or Schneiderian membrane in the process. The procedure is based on the gradual elevation of the sinus (18) in conjunction with the gradual insertion of autograft bone, preferably a coagulum of plasma rich in growth factors, either comprising bone graft material or not. The drills and osteotomes start cutting at a distance (19) from the base of the sinus of, for example, 1.5 mm.

In this way, as can be deduced from FIG. 8, suitable blunt osteotomes, are used to introduce the bone graft by raising the floor of the sinus (18) and maintaining the integrity of the sinus membrane (21).

What is claimed is:

1. A method of preparing a dental implant site in bone, said method comprising:
   (i) piercing the hardest outer layer of the bone with a starter drill to create a hole;
   (ii) drilling the hole with an additional drill of a different diameter that has an end for connection to a surgical motor;
   (iii) expanding the hole with an atraumatic bone osteotome engaged with one of a motor-driven connector or a manual driven-connector; and
   (iv) repeating steps (ii) and (iii) one or more times to define a cavity to house dental implant, in which steps (ii) and (iii) are performed successively and alternately, and each step (ii) uses an additional drill of a different diameter and each step (iii) uses atraumatic bone osteotomes of progressive diameters;
   wherein the starter drill comprises a quadrangular-section drilling end that is shorter in length and smaller in section than the osteotomes, that pierces the hardest outer layer of the bone, and an end for engagement to the surgical motor; and
   the osteotomes each have an apical end followed by a threaded conical section and a threaded cylindrical section, with the threaded cylindrical section capped by an adjustment area in which the connectors are engaged.

2. The method of claim 1, wherein the manual-driven connector has a different cross-sectional shape than that of the motor-driven connector.

3. The method of claim 1, wherein the adjustment area of the osteotomes has a polygonal-section projection, which is capped by a cylindrical projecting section that includes a circular recess in which an O-ring seal is housed.

4. The method of claim 1, wherein both the motor-driven connector and the manual driven-connector each have an end having a blind axial recess with a polygonal section, and wherein the adjustment area of the osteotomes comprises a polygonal-section projection and an O-ring seal, said polygonal-section projection and said O-ring seal of the osteotomes being engaged in the polygonal-section blind axial recess of the connectors.

5. The method of claim 1, wherein the motor-driven connector has an extension for connection to the surgical motor.

6. The method of claim 5, wherein the manual driven-connector has a coupling area for connection to a ratchet wrench that has a shape different than the extension on the manual driven-connector.

7. The method of claim 1, wherein the osteotomes are rotary osteotomes for widening of a dental implant site.

8. A method of preparing a dental implant site in bone, said method comprising:
(i) piercing the hardest outer layer of the bone with a starter drill to create a hole;
(ii) drilling the hole using at least two additional drills of different diameters that have ends for connection to a surgical motor; and
(iii) expanding the hole using one or more atraumatic bone osteotomes of progressive diameters engaged with one of a motor-driven connector or a manual driven-connector;

wherein each drilling of step (ii) is alternated with the expanding of step (iii) and steps (ii) and (iii) are performed one or more times to define a cavity to house the implant;

the starter drill comprises a quadrangular-section drilling end that is shorter in length and smaller in section than the osteotomes, that pierces the hardest outer layer of the bone, and an end for engagement to a surgical motor;

the osteotomes each have an apical end followed by a threaded conical section and a threaded cylindrical section, with the threaded cylindrical section capped by an adjustment area in which connectors are engaged; and the connectors are either a first connector for motor-driven operation or a second connector for manual-drive operation of the osteotomes which has a different cross-sectional shape than that of the first connector.

\* \* \* \* \*